(12) United States Patent
Takei et al.

(10) Patent No.: US 11,596,464 B2
(45) Date of Patent: Mar. 7, 2023

(54) MEDICAL APPARATUS

(71) Applicant: OLYMPUS CORPORATION, Hachioji (JP)

(72) Inventors: Yusuke Takei, Hino (JP); Kazuhiro Tanaka, Hachioji (JP); Tomoyuki Takashino, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 347 days.

(21) Appl. No.: 15/930,075

(22) Filed: May 12, 2020

(65) Prior Publication Data
US 2020/0268430 A1   Aug. 27, 2020

Related U.S. Application Data

(63) Continuation of application No. PCT/JP2017/041107, filed on Nov. 15, 2017.

(51) Int. Cl.
*A61B 18/08* (2006.01)
*A61B 18/00* (2006.01)

(52) U.S. Cl.
CPC .. *A61B 18/085* (2013.01); *A61B 2018/00083* (2013.01); *A61B 2018/00095* (2013.01)

(58) Field of Classification Search
CPC ........ A61B 18/085; A61B 2018/00083; A61B 2018/00095; A61B 2018/00101; A61B 2018/1457; A61B 18/1445; A61B 18/14; A61N 7/02; Y10T 29/53204

USPC .......................................................... 29/746
See application file for complete search history.

(56) References Cited

U.S. PATENT DOCUMENTS

| 5,456,684 | A | * | 10/1995 | Schmidt | A61B 17/29 606/174 |
| 7,264,618 | B2 | * | 9/2007 | Murakami | A61N 7/02 606/45 |
| 9,949,781 | B2 | * | 4/2018 | Takashino | A61B 18/1445 |
| 2017/0000556 | A1 | | 1/2017 | Morisaki | |

FOREIGN PATENT DOCUMENTS

| WO | 2004/012615 A1 | 2/2004 |
| WO | 2011/089769 A1 | 7/2011 |
| WO | 2016/035471 A1 | 3/2016 |
| WO | 2016/171067 A1 | 10/2016 |

OTHER PUBLICATIONS

Feb. 13, 2018 International Search Report issued in International Patent Application No. PCT/JP2017/041107.
May 19, 2020 International Preliminary Report on Patentability issued in Application No. PCT/JP2017/041107.

* cited by examiner

*Primary Examiner* — Donghai D Nguyen
(74) *Attorney, Agent, or Firm* — Oliff PLC

(57) ABSTRACT

A medical apparatus includes a first jaw; a second jaw that opens and closes with the first jaw; a shaft to which the second jaw is pivotably attached; and a sliding member provided between the second jaw and the shaft, abutted to each of the second jaw and the shaft, and configured to be slidable with respect to at least one of the second jaw or the shaft.

12 Claims, 7 Drawing Sheets

US 11,596,464 B2

MEDICAL APPARATUS

CROSS-REFERENCE TO RELATED APPLICATIONS

This is a Continuation Application of PCT Application No. PCT/JP2017/041107, filed Nov. 15, 2017, the entire contents of which are incorporated herein by reference.

FIELD

The present invention relates generally to a medical apparatus that conducts treatment on a treatment target using treatment energy.

BACKGROUND

US2017/0000556A1 discloses a medical apparatus that grasps a treatment target, such as living tissue, between a pair of grasping pieces, and conducts a treatment on the grasped treatment target using treatment energy, such as a high-frequency current. In this medical apparatus, the pair of grasping pieces includes a pair of treating surfaces facing each other. An electrode is provided on each of the treating surfaces, and electric energy (high-frequency power) is supplied to each of the electrodes. Upon supply of electric energy (high-frequency power) to each of the electrodes, a high-frequency current flows between the grasping pieces through the treatment target, and the treatment target is thereby treated.

In a medical apparatus similar to the one disclosed in US2017/0000556A1, a wiper structure may be provided in either one of the grasping pieces so as to equalize grasping power applied to the treatment target. In this case, the grasping piece provided with such a wiper structure includes a jaw and a swing unit. The swing unit is swingably attached to the jaw through a pin. An electrode is provided in the swing unit. Electric energy (high-frequency power) is supplied to the electrode through the jaw and the pin. In a treatment with a use of such a medical apparatus, the jaw constitutes a part of an electric path for supplying electric energy to the electrode, and for this reason, heat is often generated in the jaw. Moreover, heat generated in the electrode is often transferred to the jaw.

SUMMARY

A medical apparatus can include a first jaw; a second jaw that opens and closes with the first jaw; a shaft to which the second jaw is pivotably attached; and a sliding member provided between the second jaw and the shaft, abutted to each of the second jaw and the shaft, and configured to be slidable with respect to at least one of the second jaw or the shaft.

DETAILED DESCRIPTION

An exemplary embodiment will be described with reference to FIGS. 1 to 7.

Figure 1:
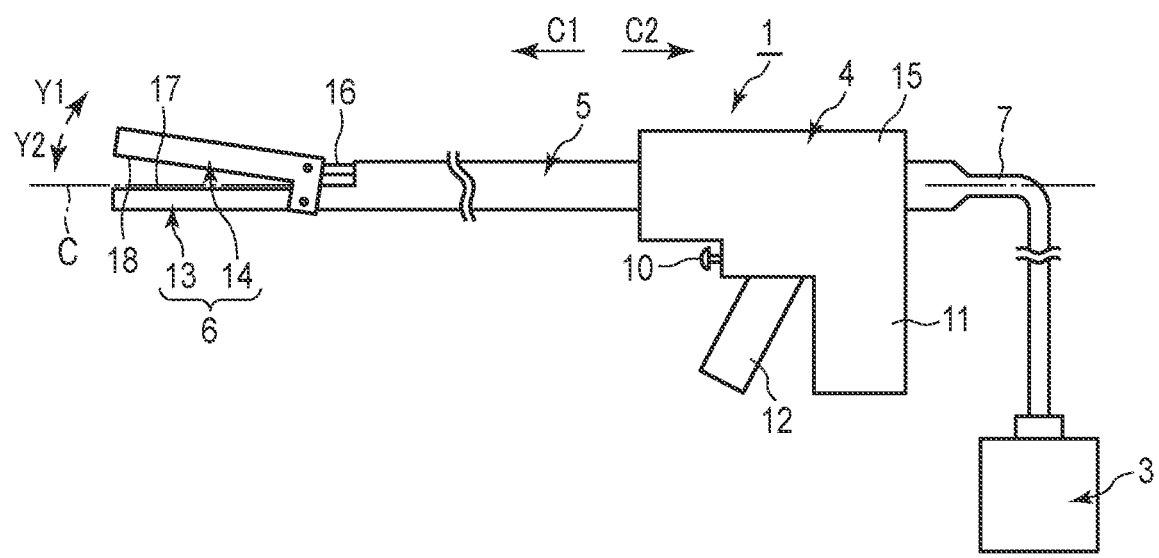
FIG. 1 schematically shows a medical apparatus according to an exemplary embodiment.

FIG. 1 shows a treatment instrument 1 which is a medical apparatus according to the present embodiment. As shown in FIG. 1, the treatment instrument 1 includes a holdable housing 4, and a cylindrical shaft 5 coupled to the housing 4. To the housing 4, one end of a cable 7 is connected. The other end of the cable 7 is detachably connected to a power supply apparatus 3.

The shaft 5 defines a longitudinal axis C. Herein, the direction along the longitudinal axis C is defined as a longitudinal direction. One side on the longitudinal direction is defined as a distal side (indicated by arrow C1 in FIG. 1), and the opposite side of the distal side is defined as a proximal side (indicated by arrow C2 in FIG. 1). The shaft 5 extends in the longitudinal axis C from the proximal side to the distal side, and is coupled to the distal side of the housing 4.

In the distal portion of the shaft 5, an end effector 6 is provided. The end effector 6 includes a first grasping piece (first jaw) 13 and a second grasping piece (second jaw) 14. The space between the first grasping piece 13 and the second grasping piece 14 can be opened and closed. In the present embodiment, the first grasping piece 13 is stationarily fixed to the shaft 5, and the second grasping piece 14 is attached to the shaft 5 in such a manner that the second grasping piece 14 can pivot relative to the first grasping piece 13. In one example, both of the first grasping piece 13 and the second grasping piece 14 are pivotably attached to the shaft 5.

The first grasping piece 13 includes a first treating surface (opposing surface) 17 facing the second grasping piece 14, and a back surface 19 facing an opposite side of the first treating surface 17. The second grasping piece 14 includes a second treating surface (opposing surface) 18 facing the first treating surface 17 of the first grasping piece 13, and a back surface 20 facing an opposite side of the second treating surface 18.

The opening and closing directions of the end effector 6 intersect with (are substantially perpendicular to) the longitudinal axis C. Of the opening and closing directions of the end effector 6, the direction in which the second grasping piece 14 opens relative to the first grasping piece 13 will be referred to as □opening direction of the second grasping piece 14□ (arrow Y1), and the direction in which the second grasping piece 14 closes relative to the first grasping piece 13 will be referred to as □closing direction of the second grasping piece 14□ (arrow Y2). Herein, the direction intersecting with (perpendicular or substantially perpendicular to) the longitudinal axis C and intersecting with (perpendicular or substantially perpendicular to) the opening and closing directions of the end effector 6 is defined as □width directions of the end effector 6□.

The housing 4 includes a housing main body 15 and a grip (fixed handle) 11. The housing main body 15 extends along the longitudinal axis C. The grip 11 extends from the housing main body 15 toward a side away from the longitudinal axis C. The shaft 5 is coupled to the housing main body 15 from the distal side.

A movable handle 12 is pivotably attached to the housing main body 15. The movable handle 12 is located on a side where the grip 11 is located with respect to the longitudinal axis C, and in the present embodiment, the movable handle 12 is located on the distal side with respect to the grip 11. When the movable handle 12 rotates relative to the housing main body 15, the movable handle 12 opens or closes with respect to the grip 11. When the movable handle 12 opens or closes with respect to the grip 11, an operation to close or open the end effector 6 in the above-described manner is input at the movable handle 12, which serves as an open/close operation inputting unit.

The movable handle 12 and the second grasping piece 14 are coupled through a movable member 16 extending through the inside of the shaft 5 along the longitudinal axis C. When the movable handle 12, which serves as an open/close operation inputting unit, is opened or closed with respect to the grip 11, the movable member 16 moves relative to the shaft 5 and the housing 4 along the longitudinal axis C, and the second grasping piece 14 pivots with respect to the shaft 5 and the first grasping piece 13. The grasping pieces 13 and 14 thus open and close in relation to each other. When the grasping pieces 13 and 14 are closed on each other in a state in which a treatment target is arranged between the grasping pieces 13 and 14, the treatment target is thereby grasped between the grasping pieces 13 and 14.

In one example, the movable handle 12 is located on the proximal side with respect to the grip 11. In another example, the movable handle 12 is located at a side opposite to the side where the grip 11 is located with respect to the longitudinal axis C, and moves in the direction intersecting with (perpendicular or substantially perpendicular to) the longitudinal axis C in the open operation and close operation.

In one example, an operation member, such as a rotative knob (not shown), etc., is attached to the housing 4. In this case, when the operation member is rotated about the longitudinal axis C with respect to the housing 4, the shaft 5 and the end effector 6 together rotate about the longitudinal axis C with respect to the housing 4.

The power source apparatus 3 has a high-frequency power source and a heat power source. The high-frequency power source includes a waveform generator, a converting circuit, and a transformer, and converts power from a battery power source or an outlet power source into high-frequency power. As will be described later, at least a part of each of the first grasping piece 13 and the second grasping piece 14 is made of an electrically conductive material. The high-frequency power source is electrically connected to each of the first grasping piece 13 and the second grasping piece 14 via an electric path provided through the inside of the cable 7, the housing 4, and the shaft 5. The high-frequency power source outputs converted high-frequency power through the above-described electric path, and supplies the high-frequency power to the first grasping piece 13 and the second grasping piece 14 as electric energy.

The heat power source includes a converting circuit and a transformer, and converts power from a battery power source or an outlet power source into a direct current or an alternating current. In at least one of the first grasping piece 13 and the second grasping piece 14, a heat source (heat emitting element) 25 (which will be described later) is provided. The heat power source is electrically connected to the heat source 25 via an electric path through the inside of the cable 7, the housing 4, and the shaft 5. The heat power source outputs converted power through the above-described electric path, and supplies electric energy to the heat source 25.

In the housing main body 15 of the housing 4, an operation button 10, which serves as an energy operation inputting unit, is provided. When an operation is input with the operation button 10 in a state in which a treatment target is grasped between the grasping pieces 13 and 14, electric energy is supplied to the end effector 6 from each of the high-frequency power source and the heat power source, and a high-frequency current and heat are applied as treatment energy to the grasped treatment target. In one example, a foot switch electrically connected to the power source apparatus 3 is provided separately from the treatment instrument 1, instead of, or in addition to the operation button 10.

In one example, a plurality of operation buttons 10 are provided in the housing 4. In a state in which a treatment target is grasped, upon an input of an operation with one of the operation buttons 10, only a high-frequency current is applied to the treatment target as treatment energy, for example. In a state in which a treatment target is grasped, upon input of an operation with another one of the operation buttons 10, a high-frequency current and heat are applied to the treatment target as treatment energy, for example.

Figure 2:
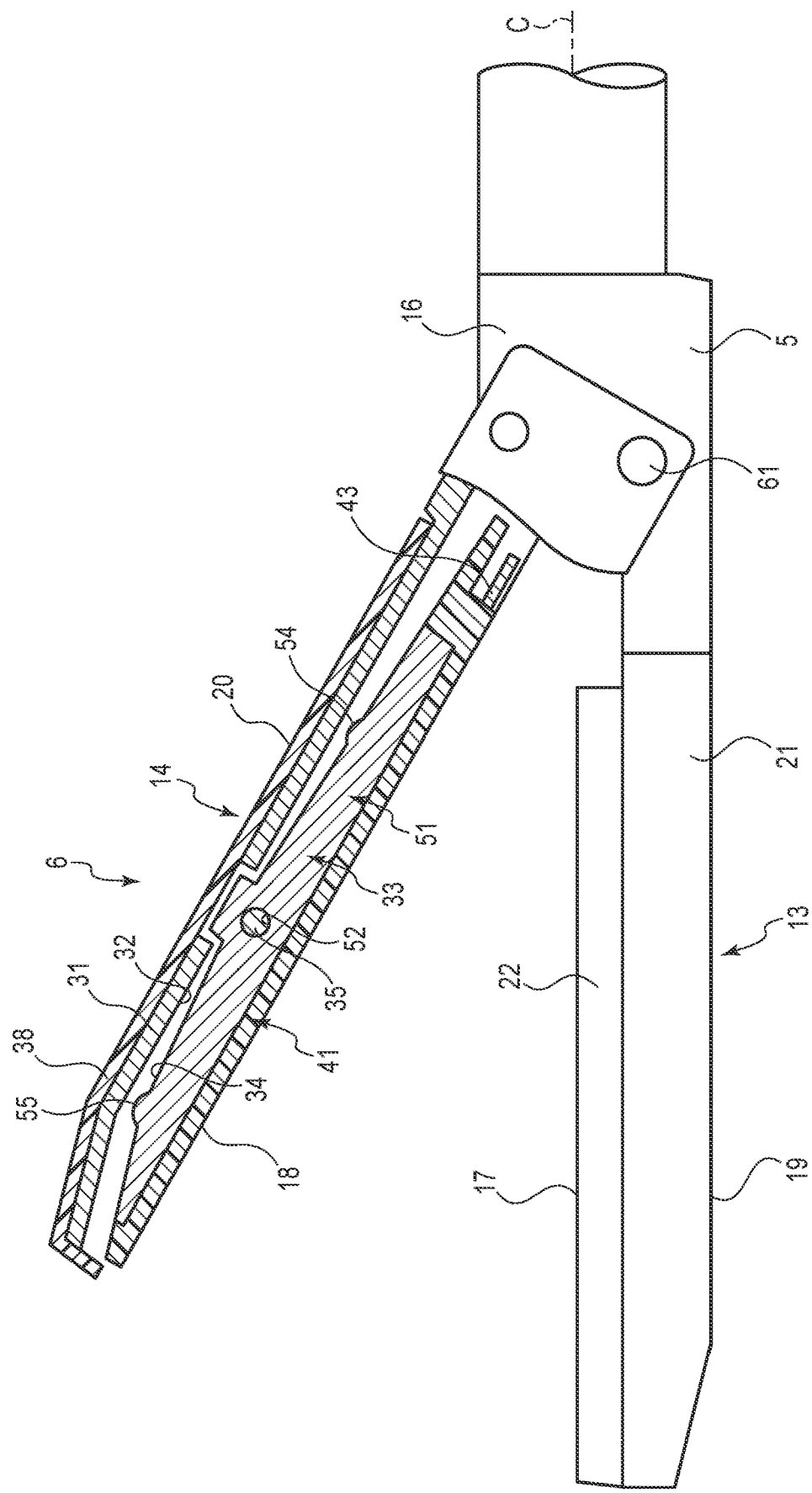
FIG. 2 is a drawing schematically showing a configuration of an end effector according to an exemplary embodiment in a cross section along a longitudinal axis.
Figure 3:
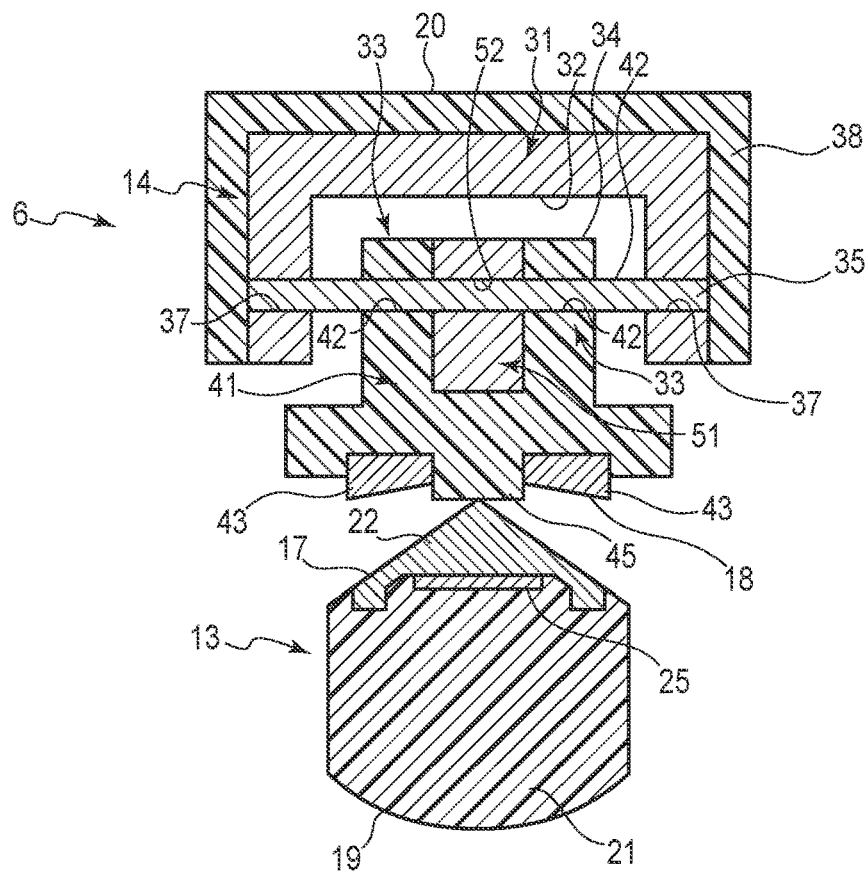
FIG. 3 is a drawing schematically showing a configuration of the end effector according to an exemplary embodiment in a cross section intersecting with a longitudinal axis.

FIG. 2 is a drawing showing the distal portion of the shaft 5 and the end effector 6. FIG. 2 is a partial cross-sectional view, taken in a cross section passing the longitudinal axis C and intersecting with (perpendicular or substantially perpendicular to) the width directions of the end effector 6. FIG. 3 is a drawing showing the state of the closed grasping pieces 13 and 14 in a cross section intersecting with (perpendicular or substantially perpendicular to) the longitudinal axis C.

As shown in FIGS. 2 and 3, the first grasping piece 13 includes a support 21 and an electrically conductive member (blade) 22. Each of the support 21 and the electrically conductive member 22 extends through the range from the proximal portion and the distal portion of the grasping piece 13 in a direction along the longitudinal axis C. The support 21 is stationarily fixed to the shaft 5. The support 21 is made of a material having electrically insulating properties and a small thermal conductivity rate. The support 21 is made of a resin, for example. The support 21 may be made by insert molding so as to encapsulate a metal core member with a resin.

The electrically conductive member 22 is attached to the support 21 from the grasping piece 14 side. The electrically conductive member 22 has electrical conductivity. The electrically conductive member 22 is made of a material having high thermal conductivity, such as a copper alloy or an aluminum alloy, for example. The electrically conductive member 22 constitutes at least a part of the first treating surface 17. In the present embodiment, the first treating surface 17 is formed in such a manner that the surface becomes closer to the grasping piece 14 side as the center of the surface is approached with respect to the width directions.

One end of the electric path consisting of electric wiring, etc. is coupled to the electrically conductive member 22. This electric path extends through the inside of the shaft 5, the housing 4, and the cable 7, and its other end is coupled to the high-frequency power source of the power source apparatus 3. It is thereby possible to electrically connect the electrically conductive member 22 to the high-frequency power source, and to supply high-frequency power from the high-frequency power source to the electrically conductive member 22 as electric energy. The electrically conductive member 22 functions as a first electrode upon supply of electric energy.

The first grasping piece 13 includes a heat source 25. The heat source 25 is attached to the electrically conductive member 22 from the side opposite to the side where the first treating surface 17 is provided. The heat source 25 is provided through the range from the proximal portion to the distal portion of the grasping piece 13 in the longitudinal direction. The heat source 25 is a heating wire attached to the electrically conductive member 22 or a heat generating pattern printed on the electrically conductive member 22, and is made of a nichrome alloy or a stainless steel alloy, for example. The heat source 25 is electrically insulated from the electrically conductive member 22.

One end of the electric path consisting of electric wire, etc. is connected to the heat source 25. The electric path extends through the inside of the shaft 5, the housing 4, and the cable 7, and the other end is connected to the heat power source of the power source apparatus 3. It is thereby possible to electrically connect the heat source 25 to the heat power source, and to supply electric energy from the heat power source to the heat source 25. Heat is generated at the heat source 25 through the supply of the electric energy from the heat power source to the heat source 25. The heat generated at the heat source 25 is transferred to the electrically conductive member 22, and is supplied to a treatment target grasped between the grasping pieces 13 and 14 from the first treating surface 17 as treatment energy.

The second grasping piece 14 includes a jaw (support) 31 and a swing unit 33. The jaw 31 and the swing unit 33 extend from the distal portion to the proximal portion of the grasping piece 14 along the direction in which the grasping piece 14 extends. The swing unit 33 is swingable with respect to the jaw 31. The jaw 31 extends along the longitudinal axis C in a state in which the grasping piece 14 is closed with respect to the grasping piece 13. In other words, the direction in which the jaw 31 extends is parallel or substantially parallel to the longitudinal axis C when the grasping piece 14 is closed with respect to the grasping piece 13. The jaw 31 has a U-shape as a cross section intersecting with (perpendicular or substantially perpendicular to) its extending direction, and the shape of the U opens toward the grasping piece 13. The jaw 31 includes an inward surface 32. The inward surface 32 faces the opposite side of the back surface 20. The jaw 31 is preferably made of a metal such as stainless steel for example, but it may be made of a resin, etc.

In the present embodiment, a cover 38 is attached to the jaw 31. The cover 38 is adhered to the jaw 31 from the back surface 20 side. The cover 38 is made of a material having a thermal conductivity rate smaller than that of the jaw 31. The cover 38 is made of a resin, for example. In the present embodiment, the cover 38 constitutes the back surface 20 of the grasping piece 14. The cover 38 is not necessarily provided.

The swing unit 33 is attached to the jaw 31 from the grasping piece 13 side. The swing unit 33 is attached to the jaw 31 via the swing pin 35. The swing pin 35 is provided in the center of the grasping piece 14 with respect to the direction in which the grasping piece 14 extends, and extends along the width directions. The swing pin 35 is made of a metal, for example. The swing unit 33 is swingable with respect to the jaw 31 about the swing pin 35 as a swing axis. The swing unit 33 constitutes the second treating surface 18 of the grasping piece 14. The swing unit 33 includes the back surface 34. The back surface 34 faces the opposite side of the second treating surface 18. The back surface 34 of the swing unit 33 faces the inward surface 32 of the jaw 31.

The swing unit 33 includes an electrode holder 41. The electrode holder 41 extends from the distal portion to the proximal portion of the jaw 31 along the direction in which the grasping piece 14 extends. The electrode holder 41 is made of a material having electrically insulating properties and a small thermal conductivity rate. The electrode holder 41 is made of a resin, for example.

An insertion hole 37 is provided in the jaw 31. The insertion hole 37 is formed along the width directions in the jaw 31. The insertion hole 37 is formed on the side walls of the jaw 31 with respect to the width directions, and penetrates the side walls of the jaw 31. An insertion hole 42 is provided in the electrode holder 41. The insertion hole 42 is formed in the electrode holder 41 along the width directions. The swing pin 35 is inserted into the insertion hole 37 of the jaw 31 and the insertion hole 42 of the electrode holder 41. With the swing pin 35 inserted into the insertion holes 37 and 42, the electrode holder 41 is attached to the jaw 31.

An electrically conductive member (second electrode) 43 is attached to the electrode holder 41. The electrically conductive member 43 is attached to the electrode holder 41 from the grasping piece 13 side. The electrically conductive member 43 extends along the direction in which the grasping piece 14 extends, and extends through the range from the distal portion to the proximal portion of the jaw 31. The electrically conductive member 43 constitutes a part of the first treating surface 17. The electrically conductive member 43 has electrical conductivity. The electrically conductive member 43 is made of a metal such as a stainless steel. The electrically conductive member 43 is electrically insulated from the jaw 31 and the swing pin 35 via the electrode holder 41. The electrically conductive member 43 has a larger thermal conductivity rate than that of the electrode holder 41. Accordingly, the electrode holder 41 has a smaller thermal conductivity rate than that of the electrically conductive member 43.

The electrode holder 41 includes an abutting portion 45. The abutting portion 45 is provided at the center of the grasping piece 14 with respect to the width directions. The abutting portion 45 projects toward the grasping piece 13 side from a space between the electrically conductive members 43. The abutting portion 45 forms a center portion of the first treating surface 17 with respect to the width directions.

In a state in which the grasping pieces 13 and 14 are closed on each other, the abutting portion 45 of the electrode holder 41 is abutted to the first treating surface 17 of the grasping piece 13. With this state, a space is formed between the electrically conductive member 22 and the electrically conductive member 43, and the electrically conductive member 43 is not brought into contact with the electrically conductive member 22. For this reason, when the electrically conductive member 22 and the electrically conductive member 43 function as electrodes, a short-circuit in an electric circuit in which high-frequency power is output from the power source apparatus 3 to the electrically conductive member 22 and the electrically conductive member 43 can be effectively prevented.

A core member 51 is attached to the electrode holder 41. The core member 51 extends in a direction in which the grasping piece 14 extends, and extends through the range from the distal portion to the proximal portion of the jaw 31. The core member 51 is arranged in the inside of the electrode holder 41. The electrode holder 41 is adhered to the core member 51 from the outer side thereof, with respect to the width directions. Accordingly, the electrode holder 41 covers at least a part of the core member 51. The core member 51 is separated from the electrically conductive member 43 via the electrode holder 41. For this reason, the core member 51 is electrically insulated from the electrically conductive member 43 via the electrode holder 41. The core member 51 is made of a material having a larger flexural strength than that of the electrode holder 41. The electrode holder 41 is made of a metal or ceramics, for example.

An insertion hole 52 is provided in the core member 51. The insertion hole 52 penetrates the core member 51 with respect to the width directions. The swing pin 35 is inserted into the insertion hole 52. In other words, the swing pin 35 penetrates the core member 51. The core member 51 is, together with the electrode holder 41, supported by the jaw 31, via the swing pin 35. The core member 51 is swingable together with the electrode holder 41, with respect to the jaw 31. The electrode holder 41 has projections provided on both sides of the core member 51 with respect to the width directions, and in the electrode holder 41, the projections project toward the jaw 31. Furthermore, the insertion hole 42 is formed in each of the projections, and penetrates the projection.

The core member 51 includes the projections 54 and 55. The projections 54 and 55 project toward the inward surface 32 of the jaw 31 from the back surface 34 of the swing unit 33. The projection 54 is provided closer to the proximal side than the swing axis (35) with respect to the direction in which the grasping piece 14 extends. The projection 54 is abutted to the inward surface 32 of the jaw 31 when a portion located closer to the proximal side than the swing axis (35) in the swing unit 33 becomes close to the jaw 31. The projection 55 is provided closer to the distal side than the swing axis (35) with respect to the direction in which the grasping piece 14 extends. The projection 55 is abutted to the inward surface 32 of the jaw 31 when a portion located closer to the distal side than the swing axis (35) in the swing unit 33 becomes close to the jaw 31.

With the above-described configuration, in a portion abutted to the jaw 31 when the swing unit 33 swings with respect to the jaw 31, the core member 51 is exposed from the electrode holder 41. For this reason, when the swing unit 33 is abutted to the jaw 31, the core member 51 is in contact with the jaw 31. In other words, in the swing unit 33, the core member 51 constitutes the portion abutted to the jaw 31.

Figure 4:
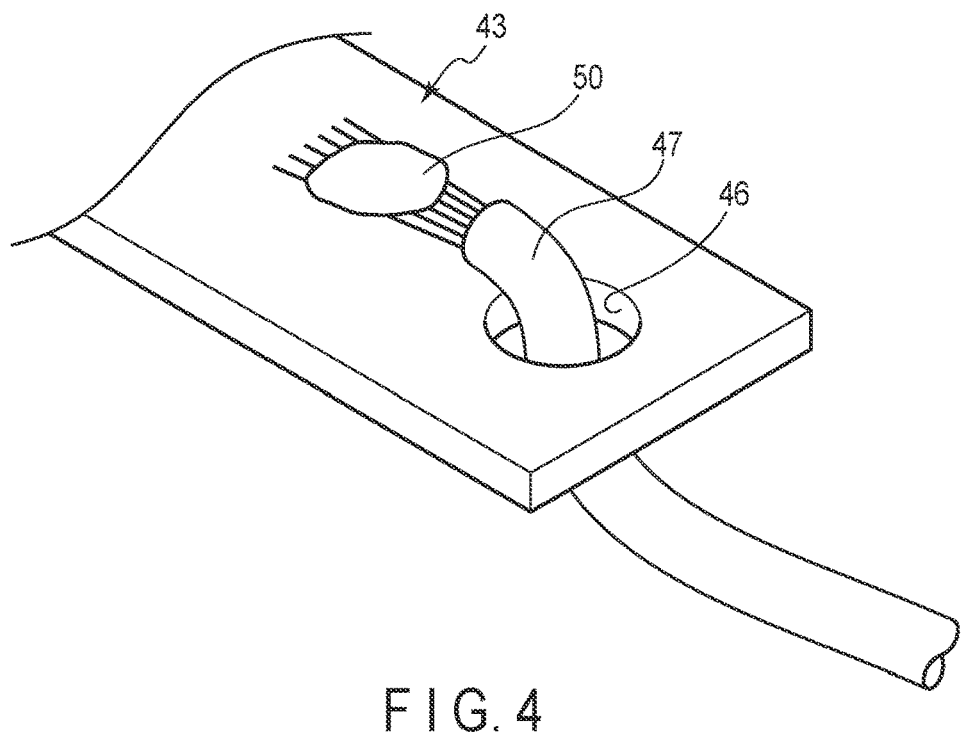
FIG. 4 is a perspective view schematically showing a connecting portion between a second electrode and electric wiring according to an exemplary embodiment.
Figure 5:
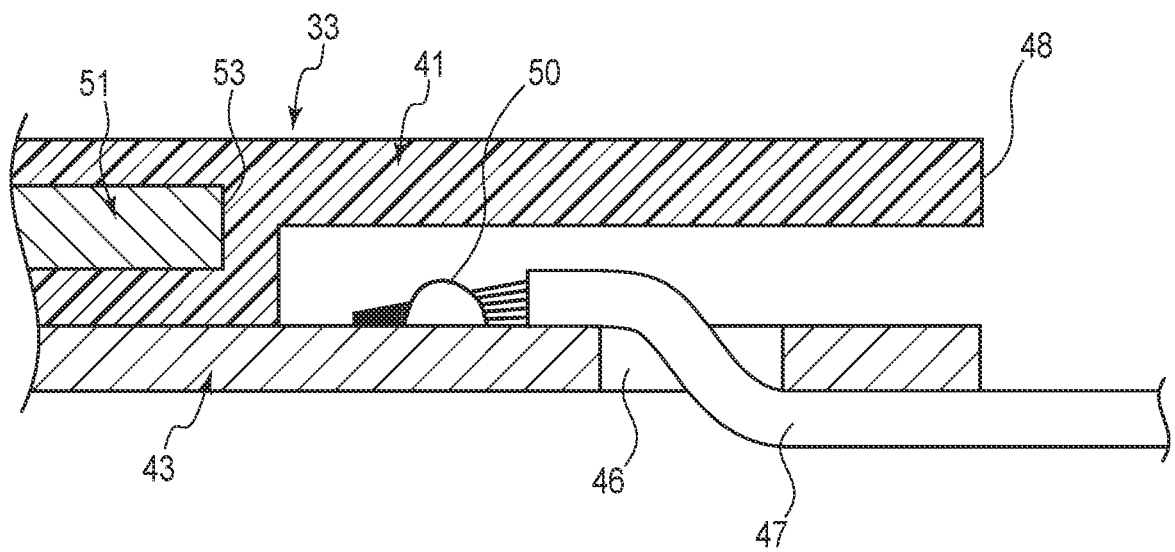
FIG. 5 is a drawing schematically showing the connecting portion between the second electrode and the electric wiring according to an exemplary embodiment in a cross section intersecting with the width directions.

FIGS. 4 and 5 are drawings showing the proximal portion of the swing unit 33. FIG. 4 is a perspective view, and FIG. 5 is a cross-sectional view, showing a cross section perpendicular or substantially perpendicular to the width directions. As shown in FIGS. 4 and 5, one end of the electric wiring (lead wire) 47 is connected to the proximal portion of the electrically conductive member 43. This electric wiring 47 extends through the inside of the shaft 5, the housing 4, and the cable 7, and its other end is electrically coupled to a high-frequency power source of the power source apparatus 3. It is thereby possible to electrically connect the electrically conductive member 43 to the high-frequency power source, and to supply high-frequency power from the high-frequency power source to the electrically conductive member 43 as electric energy. The electrically conductive member 43 functions as a second electrode upon supply of electric energy.

An insertion hole 46 is formed in the proximal portion of the electrically conductive member 43. The insertion hole 46 penetrates the electrically conductive member 43, from the second treating surface 18 side toward the back surface 20 side. The insertion hole 46 is located in the vicinity of the connecting portion 50 which connects the electric wiring 47 to the electrically conductive member 43. The electric wiring 47 extends from the inside of the shaft 5 toward the distal side, and is inserted into the insertion hole 46.

The power source apparatus 3 outputs high-frequency power as electric energy from the high-frequency power source, based on an operation at the operation button 10. The output high-frequency power is supplied to the electrically conductive member 22 of the grasping piece 13 via the aforementioned electric path, and is supplied to the electrically conductive member 43 of the grasping piece 14 via the aforementioned electric path. The electrically conductive member 22 and the electrically conductive member 43 thereby function as different electrodes having different potentials. When the electrically conductive member 22 and the electrically conductive member 43 function as electrodes in the state in which a treatment target is grasped between the grasping pieces 13 and 14, a high-frequency current flows between the electrically conductive member 22 and the electrically conductive member 43 via the treatment target, and the high-frequency current is applied to the treatment target as treatment energy.

The electrode holder 41 is provided through a range of an area closer to the proximal side than the core member 51 with respect to a direction in which the grasping piece 14 extends. Accordingly, the proximal end 48 of the electrode holder 41 is located closer to the proximal side than the proximal end 53 of the core member 51. The proximal end 48 of the electrode holder 41 is located closer to the proximal side than the connecting portion 50 that connects the electrically conductive member 43 and the electric wiring 47.

The core member 51 extends in the direction in which the grasping piece 14 extends, up to the position closer to the distal side than the connecting portion 50 that connects the electrically conductive member 43 to the electric wiring 47. Thus, the proximal end 53 of the core member 51 is located closer to the distal side than the connecting portion 50.

Figure 6:
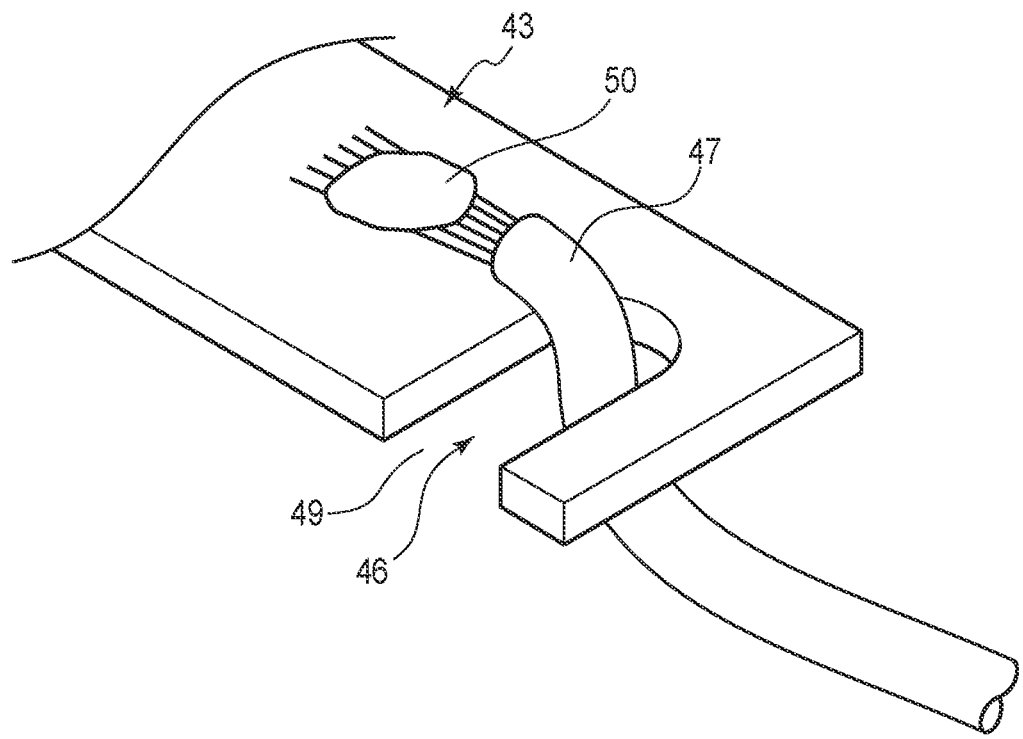
FIG. 6 is a perspective view schematically showing a connecting portion between the second electrode and the electric wiring according to a modification of an exemplary embodiment.

As shown in a modification of FIG. 6, the insertion hole 46 may have an opening 49 that opens in one of the width directions. In this case, when the electric wiring 47 is connected to the electrically conductive member 43, the electric wiring 47 can be inserted into the insertion hole 46 through the opening 49.

Figure 7:
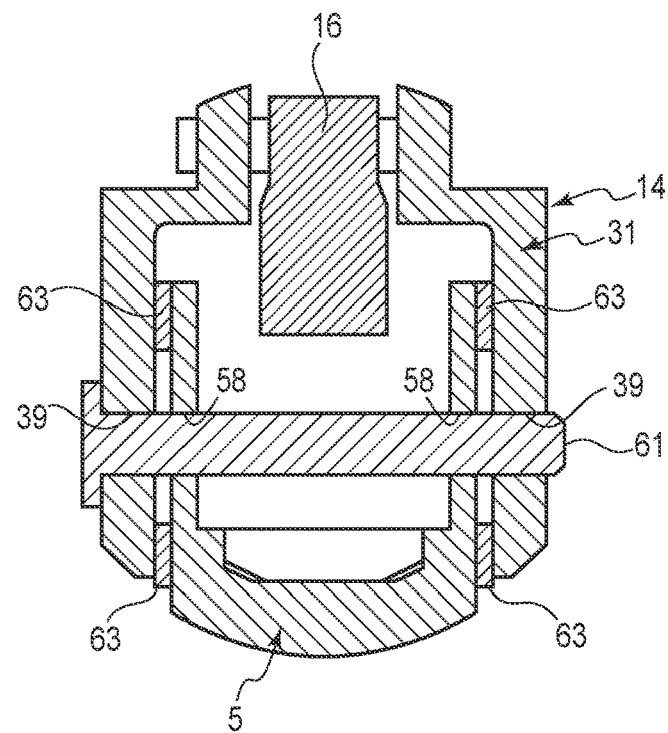
FIG. 7 is a drawing schematically showing a coupling structure between a shaft and a second grasping piece according to an exemplary embodiment in a cross section intersecting with a longitudinal axis.

FIG. 7 is a drawing showing a coupling structure between the shaft 5 and the second grasping piece 14. As shown in FIG. 7, in the distal end of the shaft 5, the cross section intersecting with (substantially perpendicular to) the longitudinal axis C has a U-shape which opens toward the second grasping piece 14. The cross section intersecting with (substantially perpendicular to) the direction in which the grasping piece 14 extends in the proximal portion of the jaw 31 of the second grasping piece 14 has a U-shape which opens toward the shaft 5 side (the first grasping piece 13 side). The second grasping piece 14 is located on both external sides of the shaft 5 with respect to the width direction. At this time, the surface facing outwardly with respect to the width directions in the shaft 5 and the surface facing inwardly with respect to the width directions in the second grasping piece 14 are opposed to each other, in a separated state.

An engagement hole 58 is formed in the distal portion of the shaft 5. The engagement hole 58 is formed in the distal portion of the shaft 5 with respect to the width directions. In the distal portion of the shaft 5, the engagement hole 58 is provided on both side walls (side surfaces) with respect to the width directions, and penetrates the side wall of the shaft 5. An engagement hole 39 is formed in the proximal portion of the jaw 31 of the second grasping piece 14. The engagement hole 39 is formed in the jaw 31 along the width directions. The engagement hole 39 is provided on each of the side walls (side surfaces) of the proximal portion of the jaw 31, and penetrates the side wall of the jaw 31.

A rotational pin 61 is inserted into the engagement hole 58 and the engagement hole 39. The rotational pin 61 extends along the width directions, and is inserted into each of the engagement hole 58 and the engagement hole 39. With the rotational pin 61 inserted into the engagement holes 58 and 39, the second grasping piece 14 is pivotably attached to the distal portion of the shaft 5.

A washer 63 is arranged between the shaft 5 and the second grasping piece 14. The washer 63 is a ring-shaped thin metal plate, and has thermal conductivity. A rotational pin 61 is inserted into the washer 63. It is preferable that the washer 63 be located at a position where the washer 63 is not in contact with the rotational pin 61. In the present embodiment, the washer 63 is a spring washer having elasticity. The washer 63 is an example of a sliding member.

The washer 63 is abutted to each of the shaft 5 and the second grasping piece 14. The washer 63 is energized by the shaft 5 and the second grasping piece 14, and is slidable with respect to each of the shaft 5 and the second grasping piece 14. The washer 63 can transfer heat between the second grasping piece 14 and the shaft 5.

The first grasping piece 13 is supported by the shaft 5. For this reason, heat generated in the heat source 25 is transferred to the shaft 5 via the first grasping piece 13. For this reason, with the washer 63 provided between the shaft 5 and the second grasping piece 14, heat is transferred between the first grasping piece 13 and the second grasping piece 14 via the washer 63 and the shaft 5.

Next, operations and advantageous effects of the treatment instrument 1 will be described. When treatment is conducted with a use of the treatment instrument 1, the end effector 6 is inserted into a body cavity, such as an abdominal cavity. Then, a treatment target, such as blood vessels, is placed between a pair of grasping pieces 13 and 14, and the end effector 6 is operated to close. The treatment target is thereby grasped between the grasping pieces 13 and 14. At this time, the treatment target is grasped between the first treating surface 17 and the second treating surface 18 provided on the swing unit 33. The swing unit 33 is swingable with respect to the jaw 31 about the swing pin 35 as a center. For this reason, even when the distal portion of the second treating surface 18 is abutted to the treatment target, the grasping force to grasp the treatment target between the grasping pieces 13 and 14 becomes substantially equal compared to the case where the proximal portion of the second treating surface 18 is abutted to the treatment target. In other words, even when the position where the second treating surface 18 is abutted to the treatment target in the direction in which the grasping piece 14 extends has been changed, the grasping force can be maintained substantially same between the grasping pieces 13 and 14.

In the state in which the treatment target is grasped between the grasping pieces 13 and 14, when an operation to supply electric energy from the power source apparatus 3 to the treatment instrument 1 is input, at least one of a high-frequency current or heat from the heat source 25 is applied, in a manner described in the above, to the treatment target grasped between the grasping pieces 13 and 14 as treatment energy.

In the present embodiment, electric energy (high-frequency power) is supplied to the electrically conductive member 43 via the electric wiring 47. The jaw 31 and the core member 51 are electrically insulated from the electrically conductive member 43 of the grasping piece 14 through the provision of the electrode holder 41. Accordingly, electric energy (high-frequency power) is supplied to the electrically conductive member 43, without involving the jaw 31. In other words, the jaw 31 is electrically insulated from the electric path that supplies electric energy (high-frequency power) to the electrically conductive member 43. For this reason, even in the state where electric energy (high-frequency power) is supplied to the electrically conductive member 43, electric energy (high-frequency power) is not supplied to the jaw 31 and the swing pin 35. For this reason, heat generated in the jaw 31 can be suppressed compared to the case where the jaw 31 constitutes a part of the electric path.

In the present embodiment, the electrode holder 41 is made of a material having a low thermal conductivity rate. For this reason, the heat generated in the electrically conductive member 43 at the time when high-frequency power is supplied is prevented from being transferred to the jaw 31 via the electrode holder 41 and the swing pin 35.

In the present embodiment, the core member 51 is provided in the swing unit 33, and the core member 51 extends in the direction in which the grasping piece 14 extends. The core member 51 is made of a material having a larger flexural strength (tensile strength). For this reason, even when the electrode holder 41 is made of a material having a low thermal conductivity rate, such as a resin, degradation of flexural strength in the swing unit 33 can be inhibited because of the provision of the core member 51. It is thereby possible to inhibit a transfer of heat to the jaw 31 and to maintain durability of the swing unit 33.

The swing unit 33 swings with respect to the jaw 31 and is abutted to the jaw 31; as a result, power acts on the portion abutted to the jaw 31. In the present embodiment, the core member 51 constitutes the portion abutted to the jaw 31 in the swing unit 33. For this reason, even if the electrode holder 41 is made of a material having a low thermal conductivity rate, such as a resin, the durability of the swing unit 33 can be further secured.

In the present embodiment, the cover 38 made of a material having a low thermal conductivity rate is attached to the jaw 31. The cover 38 constitutes the back surface 20 of the grasping piece 14. For this reason, an influence of remnant heat from the back surface 20 of the grasping piece 14 on treatment can be prevented.

In the present embodiment, the proximal end 53 of the core member 51 is arranged closer to the distal side than the connecting portion 50 that connects the electrically conductive member 43 to the electric wiring 47. Thus, a contact between the core member 51 and the electric wiring 47 is prevented, and workability at the time of connecting the electric wiring 47 to the electrically conductive member 43 is improved.

Furthermore, in the present embodiment, the electric wiring 47 is directly connected to the electrically conductive member 43, and electric energy (high-frequency power) is supplied to the electrically conductive member 43 without involving the jaw 31. In this case, the jaw 31 pivots with respect to the shaft 5, and the swing unit 33 swings with respect to the jaw 31. At this time, a force that peels off the electric wiring 47 from the electrically conductive member 43 (peel strength) acts on the connecting portion 50. Since the strength of the electric wiring 47 is especially weak in the connecting portion 50, it is desirable to reduce a force acting on the electric wiring 47 in the connecting portion 50. In the present embodiment, the electric wiring 47 is connected to the electrically conductive member 43, being inserted into the insertion hole 46. For this reason, the electric wiring 47 is connected to the electrically conductive member 43 in the connecting portion 50, being fixed to the electrically conductive member 43. For this reason, the power acting on the electric wiring 47 in the connecting portion 50 is reduced when the swing unit 33 swings with respect to the jaw 31, and prevents breaking of the electric wiring 47 and escaping of the electric wiring 47 from the electrically conductive member 43.

In the present embodiment, a washer 63 is provided between the shaft 5 and the second grasping piece 14. The washer 63 is a spring washer, and makes the sliding of the second grasping piece 14 against the shaft 5 smooth. With the washer 63 provided, heat is transferred between the first grasping piece 13 and the second grasping piece 14 via the washer 63 and the shaft 5. In the present embodiment, remnant heat in the first grasping piece 13 caused by the heat generation at the heat source 25 is dispersed to the second grasping piece 14, via the shaft 5 and the washer 63. Through the transfer of the remnant heat (an accumulated heat amount) in the first grasping piece 13 to the second grasping piece 14, the remnant heat in the first grasping piece 13 is reduced. Furthermore, remnant heat is equalized in the end effector 6, and the decrease rate of the remnant heat in the end effector 6 is thereby improved.

In one example, the swing pin 35 and the core member 51 are integrally formed. In this case, the core member 51 includes a projection projecting outwardly in the width directions, and this projection functions as the swing pin 35.

In another example, the swing unit 33 is attached to the cover 38, with the swing pin 35 involved. In this case, an insertion hole into which the swing pin 35 is inserted is formed in the cover 38, and the swing pin 35 is inserted through the cover 38 and the swing unit 33. Furthermore, the swing unit 33 is supported by the inside of the jaw 31 in such a manner that the swing unit 33 is swingable with respect to the cover 38.

In another example, ultrasonic vibration is used as a treatment energy instead of heat. In this case, an ultrasonic transducer is provided in the inside of the housing main body 15, and the ultrasonic transducer is electrically connected to the power source apparatus 3. At the distal end of the ultrasonic transducer, a vibration transmitting member (rod member) is connected. The vibration transmitting member extends along the longitudinal axis C, through the inside of the housing 4 and the shaft 5, and projects from the distal end of the shaft 5 toward the distal side. The projecting portion from the shaft 5 toward the distal side in the vibration transmitting member constitutes the first grasping piece 13. Upon supply of electric energy from the power source apparatus 3 to the ultrasonic transducer, ultrasonic vibration is generated in the ultrasonic transducer. The generated ultrasonic vibration is transmitted to the first grasping piece 13 via the vibration transmitting member, and applied to a grasped treatment target from the first grasping member 13.

In one example, a cutter (cold cutter) is provided in the end effector 6, instead of the heat source 25. In this case, a groove is formed in each of the first treating surface 17 of the first grasping piece 13 and the second treating surface 18 of the second grasping piece 14. The groove is provided in each of the center position with respect to the width directions in each of the first and second treating surfaces 17 and 18, and extends along a longitudinal direction (the direction in which the grasping piece 14 extends). Then, in a state in which a treatment target is grasped between the grasping pieces 13 and 14, the cutter is inserted into the aforementioned groove from the distal side, and the grasped treatment target is thereby dissected.

First Modification

Figure 8:
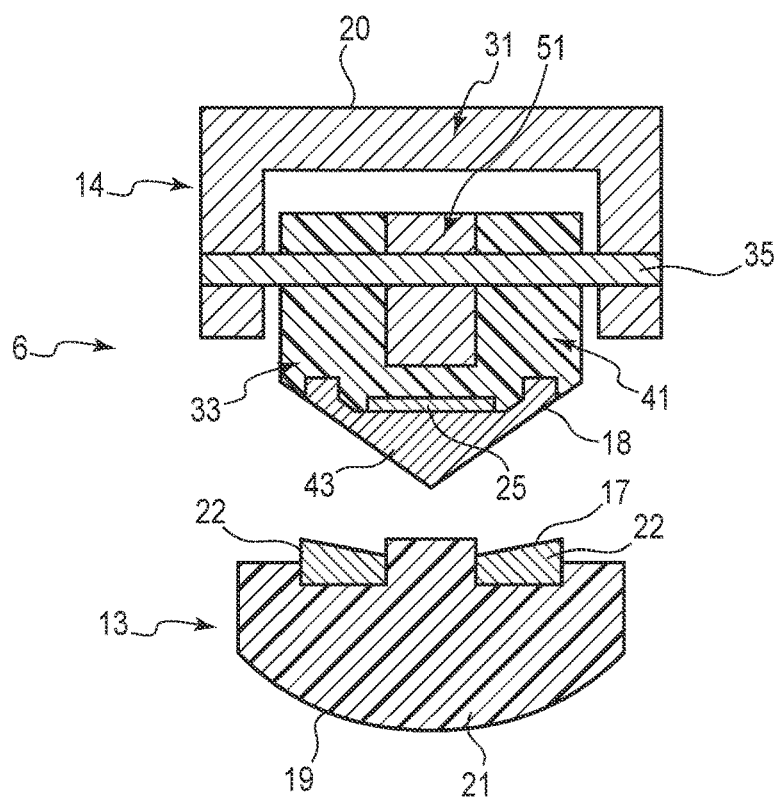
FIG. 8 is a drawing schematically showing a configuration of an end effector according to an exemplary embodiment in a cross section intersecting with a longitudinal axis.

FIG. 8 is a drawing showing a first modification. As shown in FIG. 8, the heat source 25 may be provided in the second grasping piece 14. In this case, the heat source 25 is attached in the electrically conductive member 43 from the opposite side of the second treating surface 18. The heat generated at the heat source 25 is transferred to the electrically conductive member 43, and is supplied to a treatment target grasped from the second treating surface 18.

Second Modification

Figure 9:
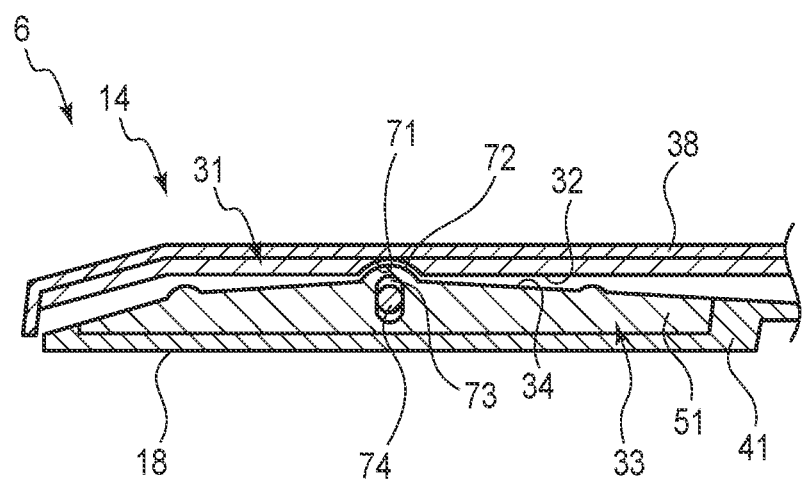
FIG. 9 is a drawing schematically showing a configuration of the second grasping piece of the end effector according to an exemplary embodiment in a cross section intersecting with width directions.

FIG. 9 is a drawing showing a second modification. As shown in FIG. 9, in the present modification, a slide groove 71 is provided on the inward surface 32 of the jaw 31, and a slide projection 72 is provided on the back surface 34 of the swing unit 33. The slide groove 71 is a concave groove recessed from the inward surface 32 of the jaw 31 toward the back surface 20, and is formed in an arc shape when seen in the cross section intersecting with (perpendicular or substantially perpendicular to) the width directions. The slide projection 72 projects from the back surface 34 of the swing unit 33 toward the back surface 20, and is formed in an arc shape when seen in the cross section intersecting with (perpendicular or substantially perpendicular to) the width directions. The slide projection 72 of the swing unit 33 engages the slide groove 71 of the jaw 31.

In each of the jaw 31 and the swing unit 33, an insertion hole 73 is formed. The insertion hole 73 penetrates each side wall (side surface) of the jaw 31 or the swing unit 33 with respect to the width directions. An anti-escape pin 74 is inserted into the insertion hole 73. The anti-escape pin 74 extends along the width directions. The insertion hole 73 is formed to be larger than the anti-escape pin 74.

In the present modification, through the insertion of the anti-escape pin 74 into the insertion hole 73, the swing unit 33 is supported by the jaw 31. Thus, the escaping, in other words, dropping, of the swing unit 33 from the jaw 31 can be prevented. With the slide projection 72 of the swing unit 33 engaging the slide groove 71 of the jaw 31, when the slide projection 72 slides with respect to the slide groove 71, the swing unit 33 swings with respect to the jaw 31.

Third Modification

Figure 10:
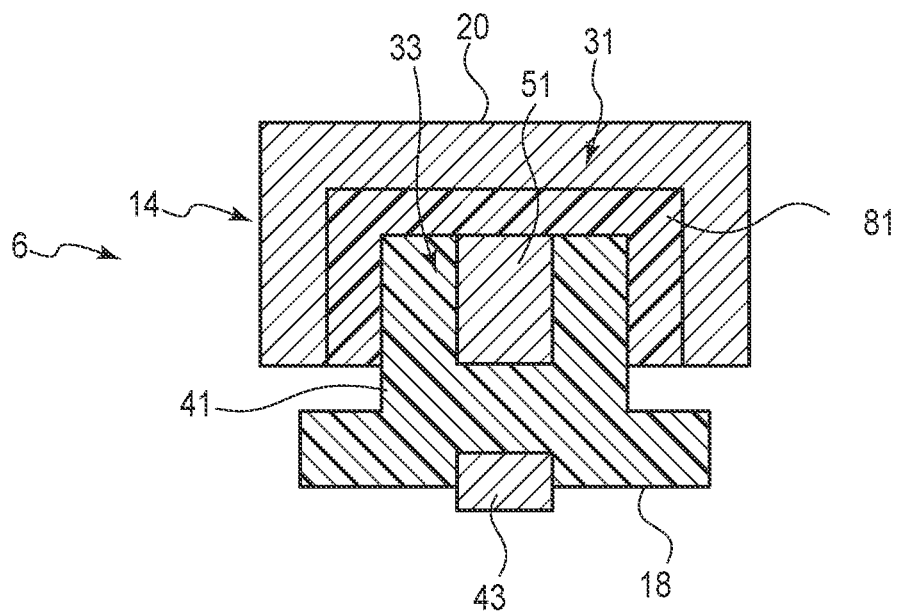
FIG. 10 is a drawing schematically showing a configuration of the end effector according to an exemplary embodiment in a cross section intersecting with a longitudinal axis.

FIG. 10 is a drawing showing a third modification. As shown in FIG. 10, in the third modification, a thermal insulating member 81 is provided between the swing unit 33 and the jaw 31. The thermal insulating member 81 has a low thermal conductivity rate, and has elasticity. A soft material such as rubber is used for the thermal insulating member 81.

In the reference example, the swing unit 33 is maintained by the thermal insulating member 81, and thereby supported by the inner side of the jaw 31. Since the thermal insulating member 81 has elasticity, the swing unit 33 becomes swingable with respect to the jaw 31. Through the arrangement of the thermal insulating member 81 between the swing unit 33 and the jaw 31, the transfer of heat from the electrically conductive member 43 to the jaw 31 is further inhibited.

REFERENCE EXAMPLES

Next, reference examples will be described with reference to FIGS. 11 and 12. Herein, the same elements as those in the embodiments, etc. of the present invention are specified by the same reference numbers, and a duplicate description of such elements will be omitted.

Figure 11:
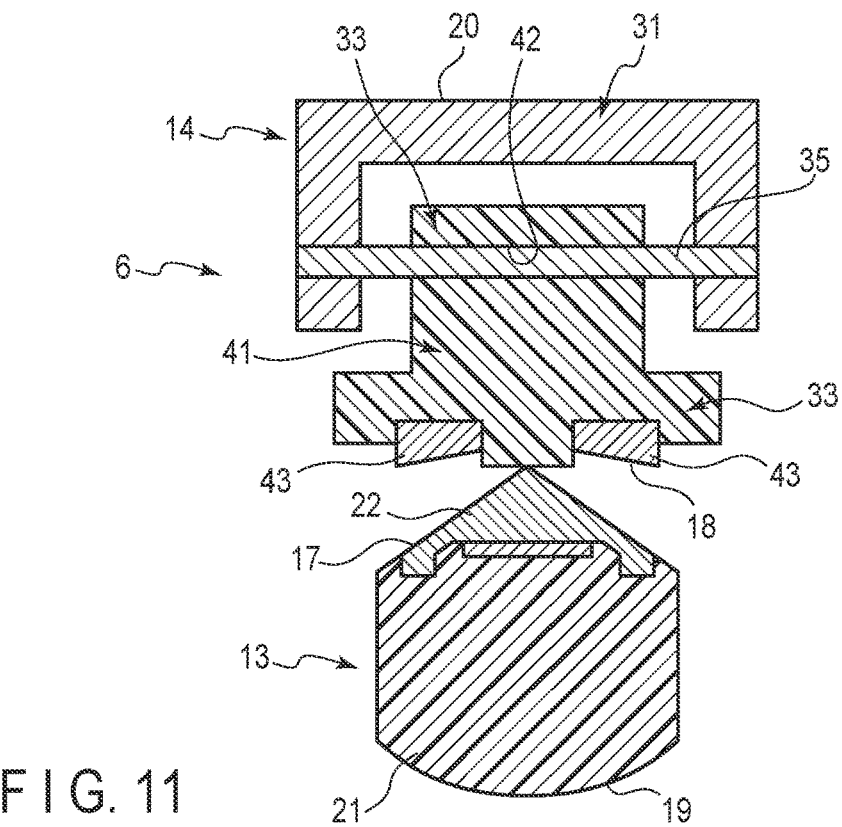
FIG. 11 is a drawing schematically showing a configuration of the end effector according to a first reference example in a cross section intersecting with a longitudinal axis.

FIG. 11 is a drawing showing a first reference example. As shown in FIG. 11, the swing unit 33 includes the electrode holder 41 and the electrically conductive member 43 in the present reference example. The electrode holder 41 is made of a material having a low thermal conductivity rate, such as a resin. One end of the electric wiring 47 is connected to the proximal portion of the electrode member 43.

Even in the present reference example, the heat generation in the jaw 31 is inhibited by the supply of electric energy to the electrically conductive member 43, without involving the jaw 31. Since the electrode holder 41 is made of a material having a low thermal conductivity rate, the transfer of heat from the electrically conductive member 43 to the jaw 31 can be inhibited.

Figure 12:
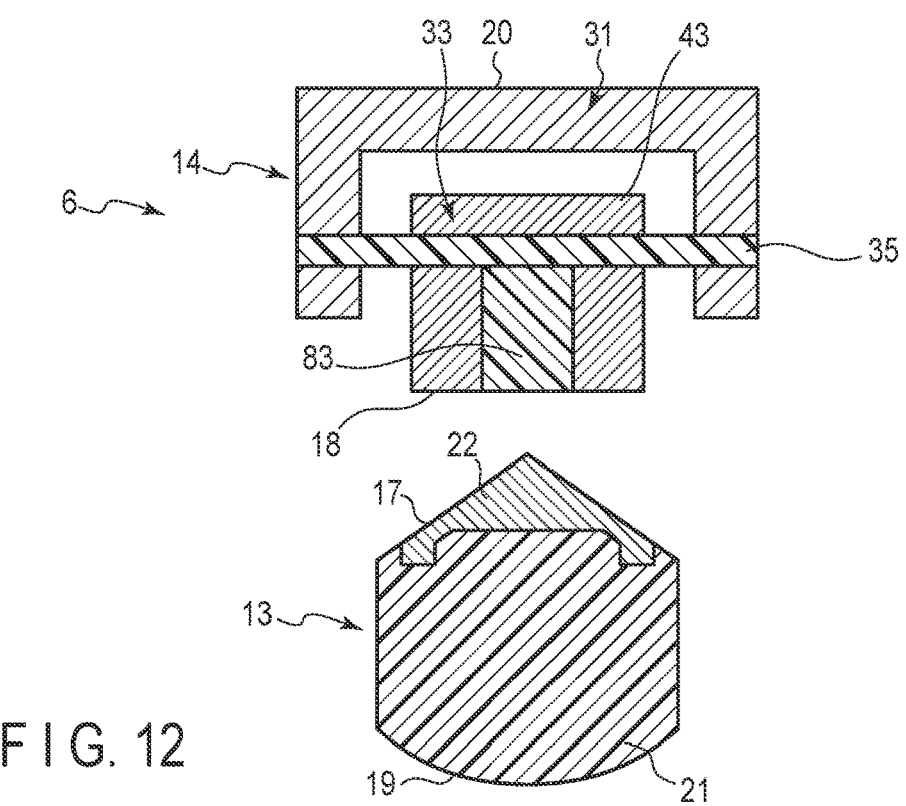
FIG. 12 is a drawing schematically showing a configuration of the end effector according to a second reference example in a cross section intersecting with a longitudinal axis.

FIG. 12 is a drawing showing a second reference example. As shown in FIG. 12, in the second reference example, the swing unit 33 includes the electrically conductive member 43 operating as a second electrode, and an insulating member 83 provided in the inside of the electrically conductive member 43. The insulating member 83 forms, in the second treating surface 18, a portion abutted to the first treating surface 17 when the grasping pieces 13 and 14 are closed on each other.

In the present reference example, the swing pin 35 has a low thermal conductivity rate, and has electric insulating properties. For example, the swing pin 35 is made of a resin. Alternatively, the swing pin 35 includes a metal pin and a resin tube encapsulating the outer surface of the pin. Alternatively, the swing pin 35 may be formed through thermal coating on the outer surface of the metal pin.

In the present reference example, the transfer of heat from the electrically conductive member 43 of the swing unit 33 to the jaw 31 can be inhibited due to the low thermal conductivity rate of the swing pin 35.

Configuration in Common Among the Embodiments Except for the Reference Examples

A medical apparatus (1) includes a first electrode (22), a jaw (31) that opens and closes with respect to the first electrode (22), a second electrode (43) that constitutes a second treating surface (18) facing the first electrode (22), an electrode holder (41) attached to the second electrode (43) in such a manner that it is swingable with respect to the jaw (31) and from an opposite side of the second treating surface (18), and having a conductivity rate lower than that of the second electrode (43), and an core member (51) provided in the electrode holder (41), electrically insulated from the second electrode (43), and having a flexural strength stronger than that of the electrode holder 41.

The present invention is not limited to the above embodiments, and can be modified in various manners in practice when implementing the invention without departing from the gist of the invention. Moreover, each of the embodiments may be implemented by being suitably combined, to a maximum extent, in which case a combined effect will be obtained. Furthermore, the above embodiments include inventions at various stages, and various inventions can be extracted by an appropriate combination of a plurality of disclosed constituent elements.

The invention claimed is:
1. A medical apparatus comprising:
a first jaw;
a second jaw that opens and closes relative to the first jaw;
a shaft to which the second jaw is pivotably attached; and
a sliding member provided between the second jaw and the shaft and configured to slide with respect to at least one of the second jaw or the shaft, wherein the sliding member transfers heat between the second jaw and the shaft.

2. The medical apparatus according to claim 1, further comprising:
a first electrode being provided on the first jaw, the first electrode including a first treating surface;
a second electrode provided in the second jaw and including a second treating surface that faces the first electrode; and
an electrode holder attached to the second jaw in such a manner that the electrode holder is configured to swing with respect to the second jaw, the electrode holder being attached to the second electrode from an opposite side of the second treating surface and having a lower thermal conductivity rate than a thermal conductivity rate of the second electrode; and
a core member provided in the electrode holder, electrically insulated from the second electrode, and having a larger flexural strength than a flexural strength of the electrode holder.

3. The medical apparatus according to claim 2, wherein:
the electrode holder has electrically insulating properties.

4. The medical apparatus according to claim 2, further comprising:
a pin that is connected to the electrode holder to the second jaw to enable the electrode holder to swing with respect to the second jaw, wherein the pin penetrates the core member.

5. The medical apparatus according to claim 4, wherein:
the pin is electrically insulated from the second electrode.

6. The medical apparatus according to claim 2, further comprising:
   electric wiring including one end that is electrically connected to the second electrode and supplies electric energy to the second electrode, wherein:
   the second electrode has an insertion hole, the electric wiring being configured to be inserted into the insertion hole.

7. The medical apparatus according to claim 6, wherein:
   a proximal portion of the electrode holder is located closer to a proximal end of the second jaw than a proximal portion of the core member, and
   a connecting portion that connects the electric wiring to the second electrode is located closer to the proximal end of the second jaw than the proximal portion of the core member.

8. The medical apparatus according to claim 2, further comprising:
   a heat-generating element provided between the electrode holder and the second electrode and configured to generate heat when electric energy is supplied to heat generating element.

9. The medical apparatus according to claim 2, further comprising:
   a heat-generating element provided in the first electrode and on an opposite side of a surface facing the second electrode, and configured to generate heat when electric energy is supplied to the heat-generating element.

10. The medical apparatus according to claim 2, wherein:
    the core member has an abutting portion configured to abut the first jaw when the electrode holder swings with respect to the second jaw.

11. The medical apparatus according to claim 2, wherein:
    the first jaw extends along a longitudinal axis, and
    the electrode holder is configured to swing with respect to the second jaw about a swing axis that intersects with the longitudinal axis.

12. The medical apparatus according to claim 1, wherein the sliding member directly abuts the second jaw and the shaft.

* * * * *